(12) United States Patent
Schilp et al.

(10) Patent No.: US 8,836,933 B2
(45) Date of Patent: Sep. 16, 2014

(54) INSPECTION DEVICE

(71) Applicant: Zimmermann & Schilp Handhabungstechnik GmbH, Regensburg (DE)

(72) Inventors: Michael Schilp, Regensburg (DE); Josef Zimmermann, Regensburg (DE); Adolf Zitzmann, Teunz (DE)

(73) Assignee: Zimmermann & Schilp Handhabungstechnik GmbH, Regensburg (DE)

( * ) Notice: Subject to any disclaimer, the term of this patent is extended or adjusted under 35 U.S.C. 154(b) by 0 days.

(21) Appl. No.: 13/898,122

(22) Filed: May 20, 2013

(65) Prior Publication Data
US 2013/0321796 A1 Dec. 5, 2013

Related U.S. Application Data

(63) Continuation of application No. 12/741,110, filed as application No. PCT/DE2008/001790 on Oct. 31, 2008, now abandoned.

(30) Foreign Application Priority Data

Nov. 1, 2007 (DE) .......................... 10 2007 052 530

(51) Int. Cl.
| | |
|---|---|
| *G01N 21/00* | (2006.01) |
| *G01N 21/88* | (2006.01) |
| *G01N 21/94* | (2006.01) |
| *G01N 21/01* | (2006.01) |
| *G01N 21/95* | (2006.01) |
| *G01N 21/03* | (2006.01) |

(52) U.S. Cl.
CPC ................ *G01N 21/88* (2013.01); *G01N 21/94* (2013.01); *G01N 21/8806* (2013.01); *G01N 21/01* (2013.01); *G01N 21/9501* (2013.01); *G01N 2021/0339* (2013.01)
USPC ..................................... 356/237.1; 356/237.2

(58) Field of Classification Search
CPC . G01N 21/9501; G02F 1/3544; G02F 1/3534; G02F 1/39; G02F 1/395; G02F 2001/392; G02F 2201/02; G02F 2203/13; G02F 1/0121; G02F 1/09; G02F 1/1334; G02F 1/1335; G02F 1/167; G02F 1/353; G02F 2001/3509
USPC .......................................... 356/237.1–237.5
See application file for complete search history.

(56) References Cited

U.S. PATENT DOCUMENTS

| | | | | |
|---|---|---|---|---|
| 5,061,679 | A * | 10/1991 | Weeks, II ....................... | 505/166 |
| 5,810,155 | A * | 9/1998 | Hashimoto et al. ............ | 198/630 |
| 6,781,684 | B1 * | 8/2004 | Ekhoff ........................ | 356/237.1 |

(Continued)

FOREIGN PATENT DOCUMENTS

| | | |
|---|---|---|
| WO | WO 2004/059695 A2 | 7/2004 |
| WO | WO 2004/076320 A1 | 9/2004 |

*Primary Examiner* — Michael P Stafira
(74) *Attorney, Agent, or Firm* — Henry M. Feiereisen LLC

(57) ABSTRACT

The invention relates to a device for inspecting contact-sensitive planar materials or workpieces, e.g. wafers for the semiconductor industry, solar cells, glasses, FPD substrates, or biologically active substrates for biosensors, as well as materials having contact-sensitive curved surfaces. Said inspection device comprises a support element (1) for supporting a material (3) on the top face of the support element (1), at least one oscillator which is connected to the support element (1) and the oscillation frequency and amplitude of which are selected in such a way as to keep the material (3) hovering on the support element (1), and at least one optical sensor (4). The support element is made of a light-permeable material, and the optical sensor (4) is arranged below the support element (1).

8 Claims, 2 Drawing Sheets

(56) References Cited

U.S. PATENT DOCUMENTS

| | | |
|---|---|---|
| 6,810,297 B2 | 10/2004 | Adin et al. |
| 2004/0174518 A1 | 9/2004 | Naiki et al. |
| 2005/0015170 A1* | 1/2005 | Adin et al. .................... 700/110 |
| 2006/0064199 A1 | 3/2006 | Zimmermann et al. |
| 2006/0115968 A1* | 6/2006 | Funk ............................ 438/530 |
| 2007/0171404 A1* | 7/2007 | Ben-Tulila et al. ......... 356/237.1 |
| 2009/0013927 A1* | 1/2009 | Yamasaki et al. ............. 118/300 |
| 2010/0264132 A1* | 10/2010 | Koelmel et al. ............... 219/647 |

* cited by examiner

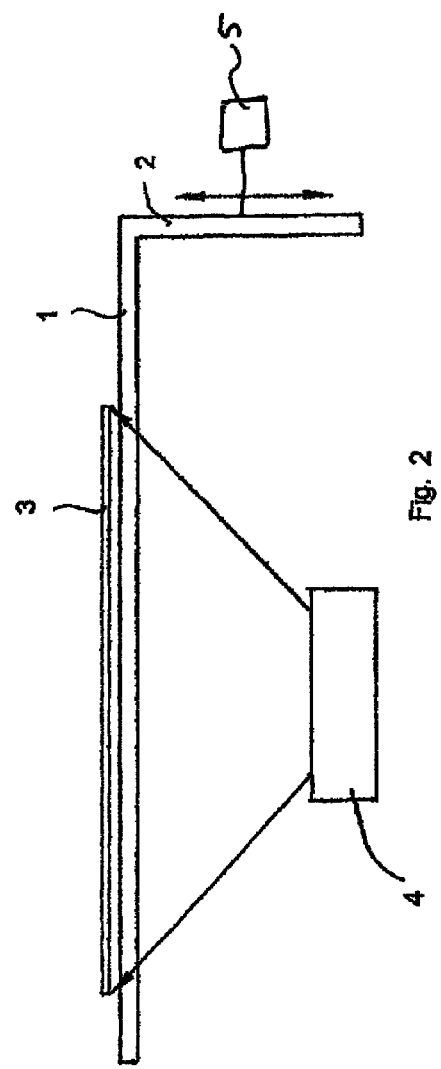

INSPECTION DEVICE

CROSS-REFERENCES TO RELATED APPLICATIONS

This application is a continuation of prior filed copending U.S. application Ser. No. 12/741,110, filed Dec. 21, 2010, the priority of which is hereby claimed under 35 U.S.C. §120, which in turn is the National Stage of International Application No. PCT/DE2008/001790, filed Oct. 31, 2008, which designated the United States and has been published as International Publication No. WO 2009/056127 and claims the priority of German Patent Application, Serial No. 10 2007 052 530.3, filed Nov. 1, 2007, pursuant to 35 U.S.C. 119(a)-(d), the contents of which are incorporated herein by reference in its entirety as if fully set forth herein.

BACKGROUND OF THE INVENTION

The invention relates to a device for inspecting contact-sensitive planar materials or work-pieces, e.g. wafers for the semiconductor industry, solar cells, glasses, FPD substrates, or biologically active substrates for biosensors, as well as materials having contact-sensitive curved surfaces. In the following, every kind of material or work-piece will be denoted as material. The surfaces of materials will be treated in different working steps, wherein treatment shall be understood to be working steps like vapor-deposition or structuring, for example. Afterwards, the result of treatment will be inspected. Inspection can be carried out by using a camera provided with an image recognition and evaluation program.

Technologies assigned for the treatment of the top surface and also of the bottom surface of the materials require both these surfaces to be inspected. The top surface of material can be inspected easily, as the material is positioned on an inspection table or a conveyer belt so that there is a free view onto the top surface thereof. However, it is very difficult to inspect the bottom surface of material at the same time, as this surface is at least partly covered by sections of the support structure so that e.g. a camera is not capable of scanning all of this surface.

For example, when a solar cell the bottom surface thereof being very sensitive to mechanical contact is transported, this solar cell is borne by several small conveyer belts. Therefore, only those areas of the bottom surface of the solar cell, which are not covered by the conveyer belts, can be inspected by a camera from below. However, when the total bottom surface of the solar cell is to be inspected, the solar cell must be removed from the conveyer belt, turned and again put onto the conveyer belt, but this is time-consuming and susceptible to trouble with continuously running processes.

In order to solve these problems, according to the prior art, the transport path is subdivided into several segments separated from each other by gaps so that the material is delivered up by the single segments. As the material is not supported at the transfer gap, the total width thereof can be scanned. However, when the material to be transported is insufficiently stiff, there is the problem that the transfer gap has to be dimensioned very small. Now and then, it is not possible to perform scanning in an unhindered way.

SUMMARY OF THE INVENTION

Therefore, it is an object of the invention to provide a technology for transporting contact-sensitive materials along a transport path and optically inspecting the bottom surfaces thereof totally without hindering the inspection to be carried out at those positions where the material is supported and thus, is covered.

This object is solved by an inspection device according to the invention and a transport and inspection device according to the invention.

The invention relates to an inspection device which comprises a support element for supporting a material to be inspected. An oscillator is connected to the support element to cause it to vibrate, wherein the oscillator frequency and the amplitude of which are selected so as to keep the material to be inspected hovering on the top side of the support element by ultrasonic levitation. The top surface of the support element is matched to the geometric shape of the bottom surface of the material.

According to the invention, the support element is made of a light-permeable material to allow the bottom surface of the material levitating on the support element to be scanned optically, that is, to be inspected by means of an optical sensor such as a camera, an interferometer, a Speckle measuring instrument or a line scan camera.

In this way, it is possible to keep contact-sensitive materials such as wafers or solar cells levitating during an inspection and to inspect the bottom surfaces thereof completely.

Depending on the light used for the inspection, it may be expedient to make the support element of a material such as glass, light-permeable ceramic material, sapphire or oscillatory light-permeable plastic material.

It will be obvious to those skilled in the art that the optical properties of the support element are dependent on the material which it is made of, on the geometric shape thereof and on the wave length of the light used for the inspection.

To transport wafers, for example, the support element is formed as a plane-parallel plate having an even surface. When optical systems have to be constructed, an expert skilled in the art will design the optical sensor thereof so that the optical properties of the plane-parallel plate with respect to the refraction of light are considered.

On the other hand, when rod-like material having a circular cross section is to be held in a non-contact way and to be inspected, the rod-like material is located in a semi-circular groove of the support element, the radius thereof corresponding to that of the rod-like material. In this case, the optical properties of the support element are different from those of a plane-parallel plate and, therefore, the refraction and reflection properties of curved surfaces have to be considered by those skilled in the art, which is true for designing the optical sensor and also for designing the illuminating system required.

Thus, the support element has to be regarded as a structural optic element which can be made by using technologies known for making and coating structural optic elements.

According to the invention, a transport and inspection device is provided, on which materials are transported along a transport path. An inspection device described above is arranged at a certain position of the transport path.

As the support plate is dependent on the shape and size of the material to be supported and the surface to be inspected may be the total surface of the material or only a section thereof, it is not possible to give concrete geometric information as to the design and shape of the support plate. It is obvious to those skilled in the art and knowing the disclosed technical science that only that surface section of the support plate, in which the propagation of light beams is not shadowed or disturbed, can be used for the inspection.

It is obvious to those skilled in the art, in which way the signals provided by an optical sensor have to be evaluated. As signal processing and evaluating is not subject-matter of the invention but known from the prior art, it is not necessary to explain it in detail for those skilled in the art.

BRIEF DESCRIPTION OF THE DRAWING

Below, the invention will be explained in detail by means of an embodiment and the enclosed schematic drawings.

FIG. 2 is a side view of the support plate shown in FIG. 1 and a camera arranged below it.

DETAILED DESCRIPTION OF PREFERRED EMBODIMENTS

Figure 1:
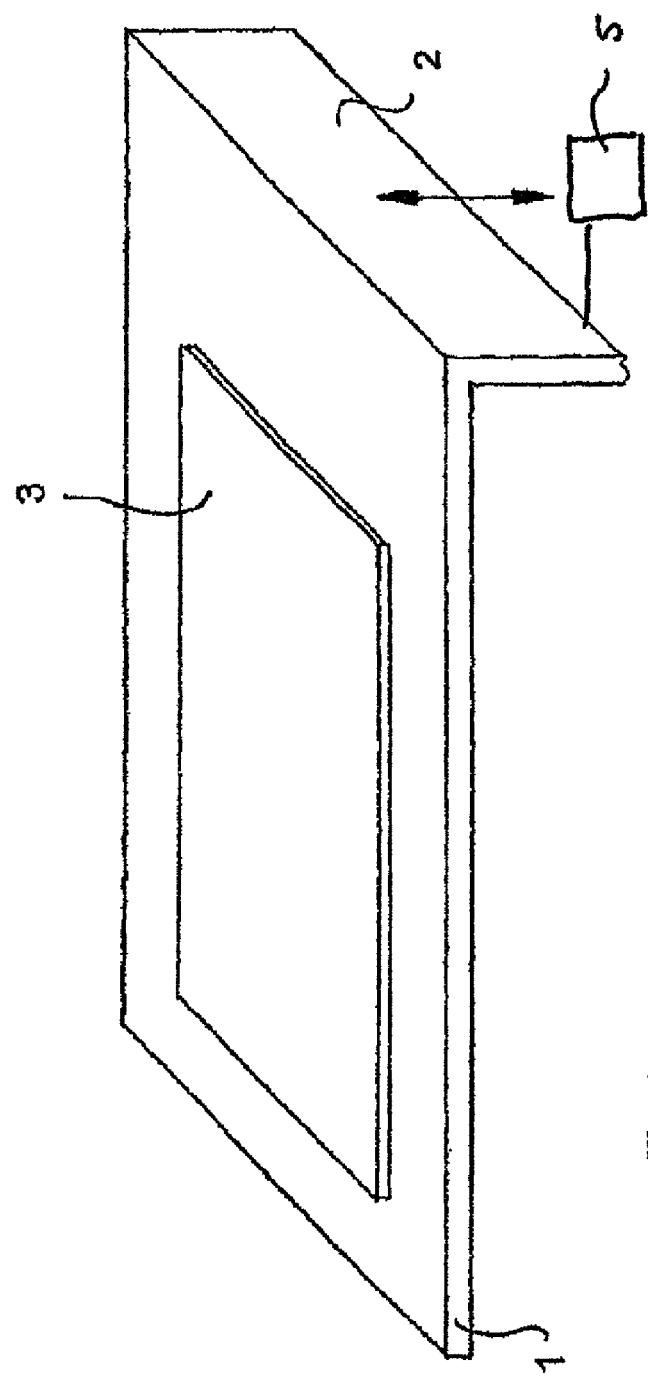
FIG. 1 is a schematic and perspective view of a support plate with a planar material put on it.

FIG. 1 is a schematic and perspective view of a support plate 1 that is bent laterally. An oscillator 5 is connected to the leg 2 of this plate. Generation of oscillation is indicated by a double arrow. The planar material 3 is a silicon wafer levitating 0.1 mm above the support plate.

FIG. 2 is a side view of the structure shown in FIG. 1. A camera 4 is arranged below the support plate 1, which is used for inspecting the bottom surface of the silicon wafer levitating on the support plate. The support plate is made of an optical glass and is laterally illuminated from below.

The invention claimed is:

1. An inspection device, comprising:
 a transparent support element having a top side and constructed for supporting a material with its bottom surface on the top side;
 at least one oscillator connected to the transparent support element for oscillating the transparent support element and having the oscillation frequency and amplitude selected to keep the material levitating on the support element; and
 an optical sensor arranged below the oscillating transparent support element and constructed for inspecting the bottom surface of the levitating material supported on the top surface of the oscillating transparent support element through the oscillating transparent support element.

2. The inspection device of claim 1, wherein the support element is made of glass.

3. The inspection device of claim 1, wherein the support element is made of a light-permeable ceramic material.

4. The inspection device of claim 1, wherein the support element is made of an oscillatory light-permeable plastic material.

5. A transport and inspection device for materials which are to be transported and inspected and are moved along a transport path by a transport device, comprising an inspection device arranged within an area of the transport path and constructed to include a transparent support element having a top side and constructed for supporting a material with its bottom surface on the top side, at least one oscillator connected to the transparent support element for oscillating the transparent support element and having the oscillation frequency and amplitude selected to keep the material levitating on the support element, and an optical sensor arranged below the oscillating transparent support element and constructed for inspecting the bottom surface of the levitating material supported on the top surface of the oscillating transparent support element through the oscillating transparent support element.

6. The transport and inspection device of claim 5, wherein the support element is made of glass.

7. The transport and inspection device of claim 5, wherein the support element is made of a light-permeable ceramic material.

8. The transport and inspection device of claim 5, wherein the support element is made of an oscillatory light-permeable plastic material.

* * * * *